(12) United States Patent
Altevogt et al.

(10) Patent No.: US 7,670,601 B2
(45) Date of Patent: Mar. 2, 2010

(54) DIAGNOSTIC AND THERAPEUTIC METHODS BASED ON THE L1 ADHESION MOLECULE FOR OVARIAN AND ENDOMETRIAL TUMORS

(75) Inventors: Peter Altevogt, Neckargemuend (DE); Mina Fogel, Gedera (IL)

(73) Assignees: Deutsches Krebsforschungszentrum Stiftung des Offentlichen Rechts, Heidelberg (DE); Mor Research Applications, Ltd., Kiryat Matalon (IL)

( * ) Notice: Subject to any disclaimer, the term of this patent is extended or adjusted under 35 U.S.C. 154(b) by 0 days.

(21) Appl. No.: 11/865,989

(22) Filed: Oct. 2, 2007

(65) Prior Publication Data

US 2008/0138331 A1    Jun. 12, 2008

Related U.S. Application Data

(62) Division of application No. 10/332,876, filed as application No. PCT/EP01/07924 on Jul. 10, 2001.

(30) Foreign Application Priority Data

Jul. 10, 2000    (EP)    .................................. 00114788

(51) Int. Cl.
*A61K 39/395*    (2006.01)
(52) U.S. Cl. .................................. 424/130.1
(58) Field of Classification Search ...................... None
See application file for complete search history.

(56) References Cited

U.S. PATENT DOCUMENTS 5,798,445 A    8/1998    Chu et al.
2004/0259084 A1    12/2004    Altevogt et al.

FOREIGN PATENT DOCUMENTS

GB    2 339 200 A    1/2000

OTHER PUBLICATIONS

Rudikoff et al (Proc Natl Acad Sci USA 1982 vol. 79 p. 1979).*
Panka et al (Proc Natl Acad Sci USA vol. 85 3080-3084 May 1988).*
Amit et al Science vol. 233 747-753 1986.*
Bristow, Robert E., "Endometrial cancer", Sep. 1999, pp. 388-393, vol. 11, No. 5.
Carreiras, Franck, et al., "Migration properties of the human ovarian adenocarcinoma cell line igrov1: importance of alpha v beta3 integrins and . . . ", "Int. J. Cancer", 1999, pp. 285-294, vol. 80.

Devita, Vincent T., et al., "Cancer: Principles and Practice of Oncology (5th Ed.)", 1997, pp. 1478-1480 and 1502, Publisher: Lippincott-Raven, Published in: New York.
Ebeling, Olaf, et al., "L1 adhesion molecule on human lyphocytes and monocytes: expression and involvement in binding to alphavbeta3 integrin", "Eur. J. Immunol.", 1996, pp. 2508-2516, vol. 26.
Fogel, Mina, et al., "L1 adhesion molecule (CD 171) in development and progression of human malignant melanoma ", "Cancer Letters", Jan. 28, 2003, pp. 237-247, vol. 189, No. 2.
Han X., et al., "Tumor lymphocytes in patients with advanced ovarian cancer: changes during in vitro culture and implications for . . . ", "Gynecologic Oncology", 1997, pp. 391-398, vol. 65.
Kadmon, Guni, et al., "The neural cell adhesion molecule N-CAM enhances L1-dependent cell-cell interactions", "The Journal of Cell Biology", Jan. 1990, pp. 193-208, vol. 110.
Kadmon, Guni, et al., "The cell adhesion molecule L1: species- and cell-type-dependent multiple binding mechanisms", "Differentiation", 1997, pp. 143-150, vol. 61.
Kadmon, Guni, et al., "L1 makes immunological progress by expanding its relations", "Developmental Immunology", 1998, pp. 205-213, vol. 6.
Katayama, Masahiro, et al., "Expression of Neural Cell Adhesion Molecule LI in Human Lung Cancer Cell Lines", "Cell Structure and Function", 1997, pp. 511-516, vol. 22, No. 5.
Loiudice, L., et al., "Ascitic fluid-associated lymphocytes in patients with metastatic ovarian cancer", "Eur. J. Gynaec. Oncol.", 1995, pp. 301-306, vol. XVI, No. 4.
Reid, Robert A., et al., "Variants of human L1 cell adhesion molecule arise through alternate splicing of RNA", "J. Mol. Neurosci.", 1992, pp. 127-135, vol. 3.
Ruenker, Annette E., et al., "The C264Y Missense Mutation in the Extracellular Domain of L1 Impairs Protein Trafficking In Vitro and In Vivo ", "J. Neuroscience", Jan. 1, 2003, pp. 277-286, vol. 23, No. 1.
Strobel, Thomas, et al., "Beta1-integrins partly mediate binding of ovarian cancer cells to peritoneal mesothelium in vitro", "Gynecologic Oncology", 1999, pp. 362-367, vol. 73.
Thies, Anka, et al., "Overexpression of the cell adhesion molecule L1 is associated with metastasis in cutaneous malignant melanoma ", "Eur. J. Cancer", Sep. 2002, pp. 1708-1716, vol. 38, No. 13.

* cited by examiner

*Primary Examiner*—Christopher H Yaen
(74) *Attorney, Agent, or Firm*—Kelly K. Reynolds; Steven J. Hultquist; Intellectual Property/Technology Law

(57) ABSTRACT

A method is described for the diagnosis of an ovarian or endometrial tumor or for a prognosis, characterized in that the L1 level is determined in a patient sample, preferably via an anti L1 antibody, the presence of L1 being an indication of the presence of an ovarian or endometrial tumor or a predisposition for such a tumor. Furthermore, methods for treating of ovarian or endometrial tumors are provided.

2 Claims, 7 Drawing Sheets

DIAGNOSTIC AND THERAPEUTIC METHODS BASED ON THE L1 ADHESION MOLECULE FOR OVARIAN AND ENDOMETRIAL TUMORS

CROSS-REFERENCE TO RELATED APPLICATIONS

This application is a divisional of and claims priority to U.S. patent application Ser. No. 10/332,876, filed May 19, 2003 and published as U.S. patent application Publication No. 2004/0259084 on Dec. 23, 2004, which claims priority of International Patent Application No. PCT/EP01/07924 filed Jul. 10, 2001 and published as WO 02/004952 on Jan. 17, 2002, which in turn claims priority of European Patent Application No. 00 114 788.3, filed Jul. 10, 2000 and published as Europeans Publication No. 1172654 on Jan. 16, 2002, the entire contents of which are incorporated by reference herein in their entirety.

BACKGROUND OF THE INVENTION

1. Field of the Invention

The present invention relates to a method for the diagnosis of an ovarian or endometrial tumor or for a prognosis, characterized in that the L1 level is determined in a patient sample, the presence of L1 being an indication of the presence of an ovarian or endometrial tumor or a possible predisposition for such a tumor. This detection is made preferably via a monoclonal anti L1 antibody or a fragment thereof. The invention also relates to pharmaceutical preparations for use in the therapy of an ovarian or endometrial tumor. Furthermore, the present invention concerns a method of treating ovarian or endometrial tumors.

2. Description of Related Art

The diagnosis of specific tumors is based inter alia on the detection of specific tumor antigens (TAG) which may originate from the cytoplasm, the cell surface and the nucleus. In this connection, a distinction is made between tissue, individual and species-specific TAGs which may also be present physiologically as differentiation antigens on cells and between TAGs which are referred to as tumor-specific neoantigens and TAGs as intermediate products of the oncogenesis of a cell type which disappear again with further differentiation. They are detectable as tumor markers by immunochemical methods, above all intracellular antigens (AG) or antigens forming (increasingly) as surface antigens on tumor cells being of interest. Of diagnostic significance are e.g. the oncofetal AG ("OFA"), e.g. the carcinoembryonal AG (in the case of colon carcinoma), the SCC AG ("squamous cell carcinoma antigen"), $\alpha_1$ fetoprotein (in the case of primary liver cell carcinoma), isoferritin and fetal sulfoglycoprotein (in the case of gastric cancer and colon carcinoma), $\alpha_2$-H ferroprotein (in the case of a malignant tumor occurring in early childhood), γ-fetoprotein (in the case of sarcomas, leukemias, breast cancers), furthermore "Tennessee AG" (tennagen), "tissue polypeptide AG" (TPA), oncofetal membrane AG (OFMA), tumor-specific transplantation AG (TSTA), membrane-associated tumor AG (MATA) as well as minor antigens such as "A-like" AG, "Forssman" AG, WGL, etc. Another tumor marker used diagnostically so far is CA125 (highly glycosylated cellular mucin which occurs in tumor cells to a greater degree and is released) which marker has been used so far for the diagnosis of human ovarian cancer or endometrial carcinoma, e.g. via the determination of the serum levels or—after operations—via the immunohistological staining of tissue samples with anti CA125 antibodies.

However, the diagnosis based on the detection of CA125 has a number of serious drawbacks. For example, increased serum levels of CA125 can also occur in a number of benignant diseases, e.g. in the case of an endometrial inflammation, pelvic inflammation, cirrhosis or also during the menstruation or a pregnancy. Increased CA125 levels are also found in the case of non-gynecologic malignant tumors such as breast cancer, colorectal cancer, pancreatic carcinoma or lung cancer. Thus, this can lead to false-positive diagnoses. CA125 is also found in the case of immunostaining of colon-adenocarcinomas, gastric cancer, lung cancer and atypical hyperplasias of the endometrium. For the early detection of ovarian or endometrial carcinoma the measurement of CA125—in combination with ultrasound—does not yield any satisfactory reliable results either. Thus, with respect to both susceptibility and specificity CA125 is not suited for an early detection of ovarian or endometrial cancer but—if at all—rather for subsequent stages or relapses, however, the above described problems regarding the specificity existing, i.e. the diagnostically hardly acceptable occurrence of false-positive findings.

SUMMARY OF THE INVENTION

Therefore, the invention is based on the technical problem of providing markers which permit an improved and more specific diagnosis of ovarian and endometrial cancers, including the possible distinction between various tumor types and the possibility of detecting metastases and thus improved therapeutic, e.g. surgical, measures. A further technical problem is to provide a therapeutic approach by using L1 as therapeutic target.

The solution to this technical problem is achieved by providing the embodiments characterized in the claims.

It has surprisingly been found that the L1 adhesion molecule represents a highly specific marker in body fluids (e.g. in the blood serum, ascites and fluid from Douglas coule de sac) and tissue from ovarian and endometrial tumors, above all for highly aggressive forms of these tumors. L1 is a neuronal adhesion molecule of 200-230 kDa, which as regards its structure belongs to the Ig superfamily. L1 is a protein associated with cell migration, which in the brain is involved in the neuronal migration in the cerebellum and in the fasciculation of neurites. L1 has several binding partners among them L1 itself, the proteoglycan neurocan and various integrins (Kadmon et al., Differentiation 61: 143-150, 1997). Soluble L1 can stimulate the migration of tumor cells and hence promote metastasis (Mechtersheimer et al., JBC 2001, in press). In the screening experiments resulting in the present invention it turned out that L1 is not expressed in normal tissues with the exception of peripheral nerves and ganglions. In benignant ovarian and endometrial tumors no L1 expression could be detected, and the screening of other malignant tumors (breast, prostate, cervix) was also negative. It showed that L1 is expressed on highly aggressive serous papilloma carcinomas of the ovary and the endometrium. Soluble L1 was detectable in the serum and ascitic or pleural fluids of tumor patients but not in normal sera and body fluids or in patients having benignant tumors. Preoperative samples which were obtained by gynecologic curettage were positive in serous papilloma carcinomas of the endometrium and with the involvement of the ovary. Thus, the expression of L1 as cell surface molecule in the serum and in body fluids is highly significant as regards the early detection of aggressive ovarian and endometrial tumors and also as regards the prognostication. Therefore, the L1 detection permits the early detection and accurate diagnosis or prognosis of aggressive ovarian and endometrial tumors.

Thus, the subject matter of the present invention relates to a method for the diagnosis of an ovarian or endometrial tumor or for a prognosis, characterized in that the L1 level is determined in a patient sample, the presence of L1 being an indication of the presence of an ovarian or endometrial tumor or a predisposition for such a tumor.

Suitable methods of obtaining a patient sample are known to a person skilled in the art. The L1 adhesion molecule can be detected via common methods, the known amino acid sequence of the L1 protein or the nucleic acid sequence of the corresponding gene being used as a basis (Reid, R. A. et al., J. Mol. Neurosci. 3: 127-135, 1992). In this connection, the detection may refer to the transcription (detection of the concentration of the mRNA via common methods) or the L1 protein per se, the latter being preferred. The expression "the presence of L1 [as] an indication of the presence of an ovarian or endometrial tumor or a predisposition for such a tumor" also comprises the situation in which the concentration of L1 is increased as compared to a control (e.g. body fluid or tissue of a healthy person).

In a first preferred embodiment of the method according to the invention the L1 level is determined by determining L1 as cell surface molecule in tissue. Suitable tissues are removed tumor tissue and cell material obtained by curettage, the tissue obtained from a gynecologic curettage being preferred.

In a second preferred embodiment of the method according to the invention the L1 level is determined by determining L1 in soluble form in a body fluid. Suitable body fluids are blood serum, ascitic or pleural fluid or fluid from Douglas coule de sac, serum being preferred.

A third preferred embodiment does not carry out the detection of L1 but the detection of L1-specific antibodies by means of (recombinant) L1. For this purpose, purified (recombinant) L1 is immobilized on the surface of microtitration plates and then incubated with patient serum. Bound antibodies are then detected by means of an enzyme-conjugated second antibody and a color reaction.

In a fourth preferred embodiment L1 mRNA is detected in a body fluid sample, preferably in blood serum.

Suitable detection methods of L1, L1 mRNA and L1 antibodies, respectively, and suitable specific probes are known to the person skilled in the art, the detection of L1 protein via specific antibodies being preferred, the same or different antibodies being usable for both the soluble form and for the form on the cell surface.

In the particularly preferred first and second embodiments of the method according to the invention the L1 level is therefore determined by contacting the patient sample with an anti-L1 antibody or a fragment thereof and then determining whether the anti-L1 antibody or the fragment thereof has been bound to L1. In this regard reference is made to FIG. 6A-C.

The antibodies suitable for this purpose may be monoclonal, polyclonal or synthetic antibodies or fragments thereof. In this connection, the expression "fragment" refers to all parts of the monoclonal antibody (e.g. Fab-, Fv- or "single chain Fv" fragments) which have the same epitope specificity as the complete antibody. The production of such fragments is known to the person skilled in the art. The antibodies according to the invention are preferably monoclonal antibodies. The antibodies according to the invention can be prepared according to standard methods, L1 or a synthetic fragment thereof, which is present in both L1 forms (soluble/anchored on the cell surface) preferably serving as an immunogen. This polypeptide or peptide and the fragment thereof, respectively, can be produced e.g. by obtaining the corresponding gene, cloning and recombinant expression. Methods of obtaining monoclonal antibodies are known to the person skilled in the art. Anti-L1 antibodies suitable for the diagnostic method according to the invention are commercially available. These are e.g. the primary human monoclonal anti L1 antibodies 15551A (Company of Pharmingen, San Diego, USA) or MCA1753 (BIOZOL Diagnostica Vertrieb GmbH, Eching, Germany).

In an even more preferred embodiment of the method according to the invention the L1 level is determined via a primary monoclonal anti-L1 antibody and a commercially available secondary antibody. The secondary antibody may carry any label which may be detected. It is, however, preferred that this secondary antibody may be biotin-conjugated and may be detected by using streptavidin peroxidase. The person skilled in the art is perfectly familiar with methods of carrying out this embodiment. The detection of L1 (e.g. via ELISA) can also achieved with only one (monoclonal) antibody since L1 in serum is multimeric (c.f. Example 3, FIG. 5B).

In a preferred embodiment the patient sample is immobilized, e.g. as paraffin section. The patient sample can also be absorbed to the wall of a plastic dish by common methods such that L1 does not loose its bonding specificity e.g. for a specific antibody added thereto.

In a preferred alternative embodiment of the method according to the invention the anti L1 antibody or the fragment thereof is immobilized, i.e. it is absorbed e.g. to the wall of a plastic dish without loosing its bonding specificity for L1. Then a patient sample is added.

The bonding of the antibody can be detected by common methods, e.g. Western blot, ELISA, radioimmunoassay (RIA), etc., RIA and ELISA being preferred.

The above mentioned preferred fourth embodiment of the method of the present invention is based on the detection of L1 mRNA by RT-PCR. It has shown before that different isoforms of human L1 (i.e. hemoatopoietic L1 vs. neural L1) can be distinguished on the basis of L1 exon 27 usage. Hematopoietic cells do not express exon 27. (Ebeling et al, Eur J Immunol. 26:2508-2516, 1996). This exon encodes 4 aminoacids in the cytoplasmic tail of L1. By RT-PCR using specific primer for this region of L1 it has now found out that ovarian tumors (established cell lines and tumor speciments) express the neural form of L1 which is characterized by an insertion of 12 nucleotides (FIG. 4). Using the same primers it has been observed that L1 specific mRNA could be detected in tumor patient sera. RT-PCR detection of tumor derived mRNA (possibly derived from tumor cells in the blood) in addition to protein detection by ELISA is a sensitive technique for diagnosis.

Based on the present invention a kit was also developed which is of use for the diagnostic method according to the invention and preferably contains an anti L1 antibody or a fragment thereof and in addition L1 or a bond-active part thereof for the purpose of control. The expression "bond-active part" refers to a fragment which reacts with the antibody with which the whole molecule reacts as well. Depending on the development of the kit, the antibody can be conjugated to another unit, e.g. a marker, and/or it can be immobilized on a solid carrier (substrate). The kit can also contain a second antibody for the detection of L1/antibody complexes. The antibody or the fragment thereof may be present in free form or be immobilized on a solid carrier, e.g. a plastic dish, a test tube, a microtitration plate, a test rod, etc. The kit may also contain instructions which describe the use of the antibody or a fragment thereof in an assay for the detection of a predisposition or the presence of a tumor. The kit can also contain suitable reagents for the detection of labelings or for the labeling of positive and negative controls, wash solutions, dilution buffers, etc.

In the case of a positive diagnostic detection of an ovarian or endometrial tumor by means of the above described anti-L1 antibodies or fragments thereof, immunotherapy via the sensibilization of tumor-specific T lymphocytes can also be carried out according to known methods with the above mentioned antibodies or fragments thereof or with peptides which are derived from L1 (on the basis of the known amino acid sequence) and have preferably a length of at least 9-12 amino acids. In addition, antibodies against L1 can also be used with the intention to use L1 as a tumor-specific target antigen.

Thus, the present invention also relates to a pharmaceutical preparation which contains an anti L1 antibody or a fragment thereof, or a peptide derived from L1, or a L1 antisense oligonucleotide.

The antibodies are preferably monoclonal antibodies. In a particularly preferred embodiment said monoclonal antibody is an antibody originating from an animal (e.g. mouse), a humanized antibody or a chimeric antibody or a fragment thereof. Chimeric antibodies resembling human antibodies or humanized antibodies have a reduced potential antigenicity, however, their affinity for the target is not lowered. The production of chimeric and humanized antibodies and of antibodies resembling human antibodies, respectively, was described in detail (see e.g. Queen et al., Proc. Natl. Acad. Sci. USA 86 (1989), 10029, and Verhoeyan et al., Science 239 (1988), 1534). Humanized immunoglobulins have variable framework regions which originate substantially from human immunoglobulin (with the designation of acceptor immunoglobulin) and the complementarity of the determining regions which originate substantially from a non-human immunoglobulin (e.g. of a mouse) (with the designation of donor immunoglobulin). The constant region(s) originate(s), if present, also substantially from a human immunoglobulin. When administered to human patients, humanized (and the human) antibodies offer a number of advantages over antibodies of mice or other species: (a) the human immune system should not regard the framework or the constant region of the humanized antibody as foreign and therefore the antibody response against such an injected antibody should be less than against a completely foreign mouse antibody or a partially foreign chimeric antibody; (b) since the effector region of the humanized antibody is human, it interacts better with other parts of the human immune system, and (c) injected humanized antibodies have a half life which is substantially equivalent to that of naturally occurring human antibodies, which permits to administer smaller and less frequent doses as compared to antibodies of other species.

In a preferred embodiment thereof, L1 mAb is labeled with (123)I for imaging and injected i.p. or i.v. as described (van-Zanten-Przybysz, I. Int. J. Cancer 92:106-114, 2001). MAb to L1 is injected after stable conjugation with cytotoxic drugs in order to kill tumor cells. Examples of such cytotoxic compounds are radionuclides, toxic proteins (e.g. saporin), chemotherapeutic agents or further antibodies with other specificity (e.g. against T cells, e.g. CD3), so that bifunctional antibodies form which effect the killing of tumor cells by means of cytotoxic T cells.

In another preferred embodiment, overexpression of L1 in ovarian and endometrium tumors can be used to prime cytotoxic T lymphocytes in order to kill tumor cells in situ.

A) Peptides derived from the sequence L1 may be used to vaccinate tumor patients. Preferably, a mixture of L1-peptides restricted by HLA-A1 (ATEGWFIGF (SEQ ID NO: 1) and GSDDSLADY (SEQ ID NO: 2)), HLA-A2 (LLANAY-IYV (SEQ ID NO: 3) and WLDEDGTTV (SEQ ID NO: 4)) and HLA-A3 (VLTGYVLSY (SEQ ID NO: 5)) in an emulsion with GM-CSF and Montanide ISA-51 adjuvant (Seppic, Fairfield, N.J., USA) are used. Patients receive a vaccine comprising the 5 L1 peptides (50-200 μg, preferably 100 μg each) and 150-200 μg (preferably 190 μg) of the HLA-DR-restricted tetanus helper peptide AQYIKANSKFIGITEL (SEQ ID NO: 6). This peptide represents peptide p2 of tetanus toxoid (residues 830-844) plus an amino-terminal alanine residue to prevent formation of pyroglutamate from the N-terminal glutamine residue. Tetanus peptide p2 is a promiscuous binder to HLA-DR molecules. Vaccines are administered with 150-250 μg preferably 225 μg) GM-CSF in Montanide ISA-51 adjuvant. Each patient is preferably immunized at days 0, 7, 14, 28, 35 and 42 for a total of 6 immunizations as described by Yamshchikov et al Int. J. Cancer 92:703 (2001). The individual time frame, doses and total number of immunizations can be determined by a medical doctor depending on the kind of tumor, tumor growth, presence/absence of metastasis and patient's data (weight, age etc.).

B) Dendritic cells derived from tumor patients may be pulsed with the above mentioned L1 peptides as described by Lau et al J. Immunother 24:66-78 (2001). The dendritic cells are preferably obtained by incubation of plastic-adherent peripheral blood mononuclear cells from tumor patients with IL-4 and GM-CSF for 8 days in serumless medium. The dendritic cells are then pulsed with L1 peptides (each at approximately 50 μg/ml) for overnight and then used for (intravenous) infusions.

In a further preferred embodiment, the overexpression of L1 in ovarial or endometrial tumors is treated with L1 antisense oligonucleotides. Since cell migration is a prerequisite of tumor cell dissemination it is adviseable to eliminate L1 from the tumor cells. This can be achieved by established antisense technology. An L1 antisense oligonucleotide is used to downregulate L1 expression in tumor cells. It corresponds preferably to the sequence AGGCTGTCGTCACT-GCCCA (SEQ ID NO: 7) and is the inverse complement of nucleotides +3593/3611 of the sequence of human L1. The phosphorothioate oligonucleotide is preferably injected into the peritoneum of the tumor patient at doses between 1-12 mg/kg to achieve significant concentrations of oligonucleotide. The individual time frame, doses and total number of administrations can be determined by a medical doctor depending on the kind of tumor, tumor growth, presence/absence of metastasis and patient's data (weight, age etc.).

BRIEF DESCRIPTION OF THE DRAWINGS

FIG. 2A: Tissue obtained from curettage. FIG. 2B: Control sections from ovarian adenocarcinoma

FIG. 5: Comparison of two different ELISA formats.

DETAILED DESCRIPTION OF THE INVENTION

The following examples explain the invention.

Example 1

Figure 1:
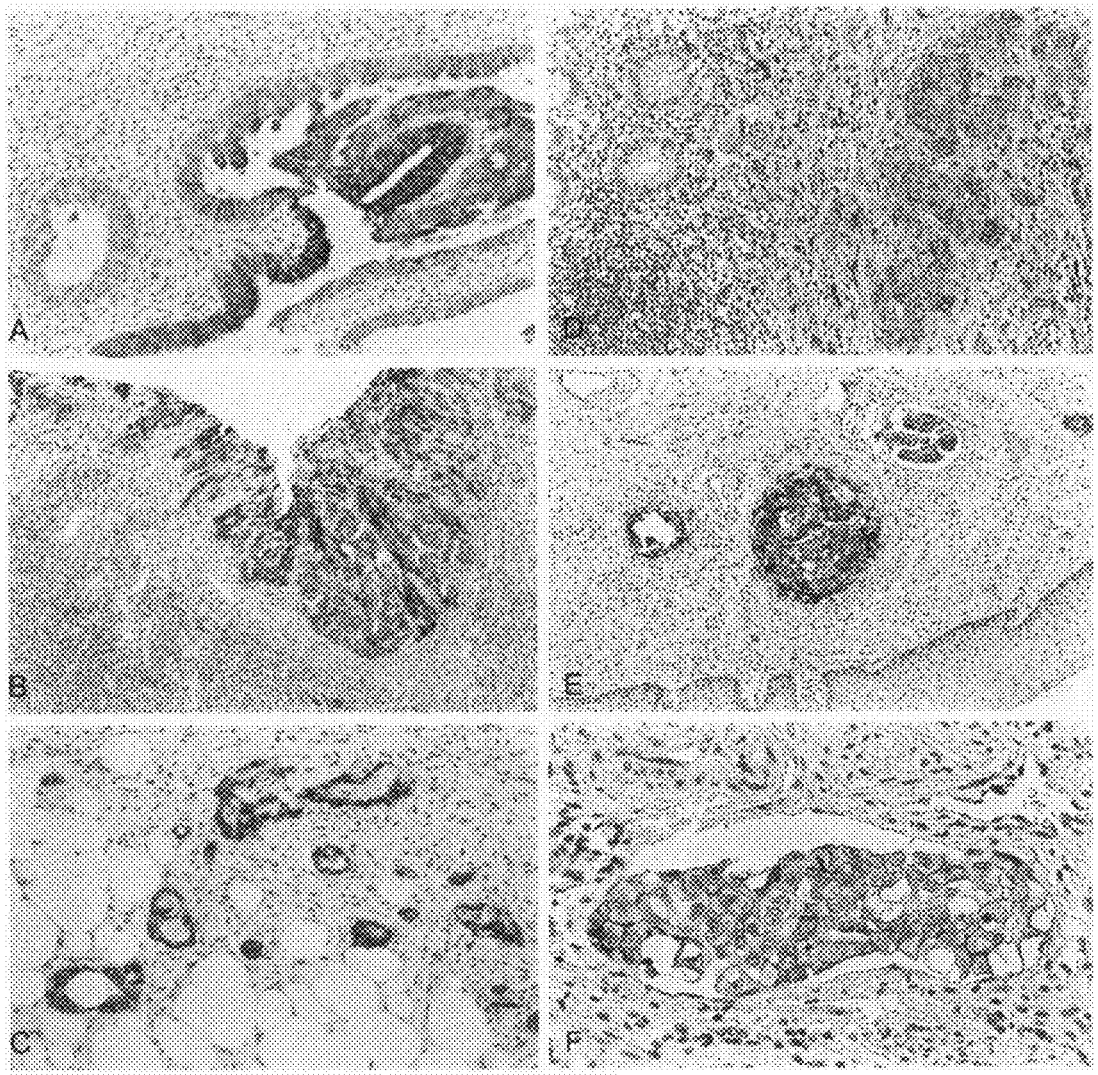
FIG. 1A: Endometroid ovarian adenocarcinoma composed of tubular glands and lined by non-mucin secreting stratified epithelium. Immunohistochemical staining with anti L1 antibody shows strong heterogenous membral staining.
FIG. 1B: Serous carcinoma of the ovary showing papillary and slit like configurations with solid tumor masses in the stroma. Strong positive immunohistochemical staining with anti L1.
FIG. 1C: Omentum with disseminated tumoral glands and desmoplastic reaction. Strong homogeneous immunostaining of tumoral cells by anti L1 antibody.
FIG. 1D: Appendical wall infiltrated by ovarian carcinoma cells. Strong homogeneous staining of tumoral cells by anti L1 antibody. No staining of normal mucosal glands and lymphatic tissue. Small peripheral nerve bundles show strong positive staining.
FIG. 1E: Vaginal wall showing small tumoral mass in the lamina propria and small tumor emboli in the dilated lmyphatics. Immunostaining with anti L1 shows strong homogeneous staining.
FIG. 1F: Ovarian carcinoma embolus in the lymphatics of the myometrium showing heterogeneous membranous staining of tumoral cell by anti L1.

The Examination of Curettage Tissue Shows a High Correlation Between the Expression of L1 and the Clinical Stage and the Pathological Degree of the Tumors, Respectively Tumor tissue is embedded in paraffin according to standard methods and serial sections are made. Following the treatment of the sections in the microwave oven (10 min., 92° C.) in the presence of 1 mmol EDTA (pH 8.0) immunostaining of the tissue is carried out by means of the MCA1753 antibody (Biozol Diagnostica Vertiebs GmbH). The bound first antibody is detected by means of an enzyme-coupled second antibody (Vector ABC Kit; www.vectorlabs.com). Some exemplary stainings are shown in FIG. 1. The clinical data are listed in Tables 1 and 2.

Figure 2:
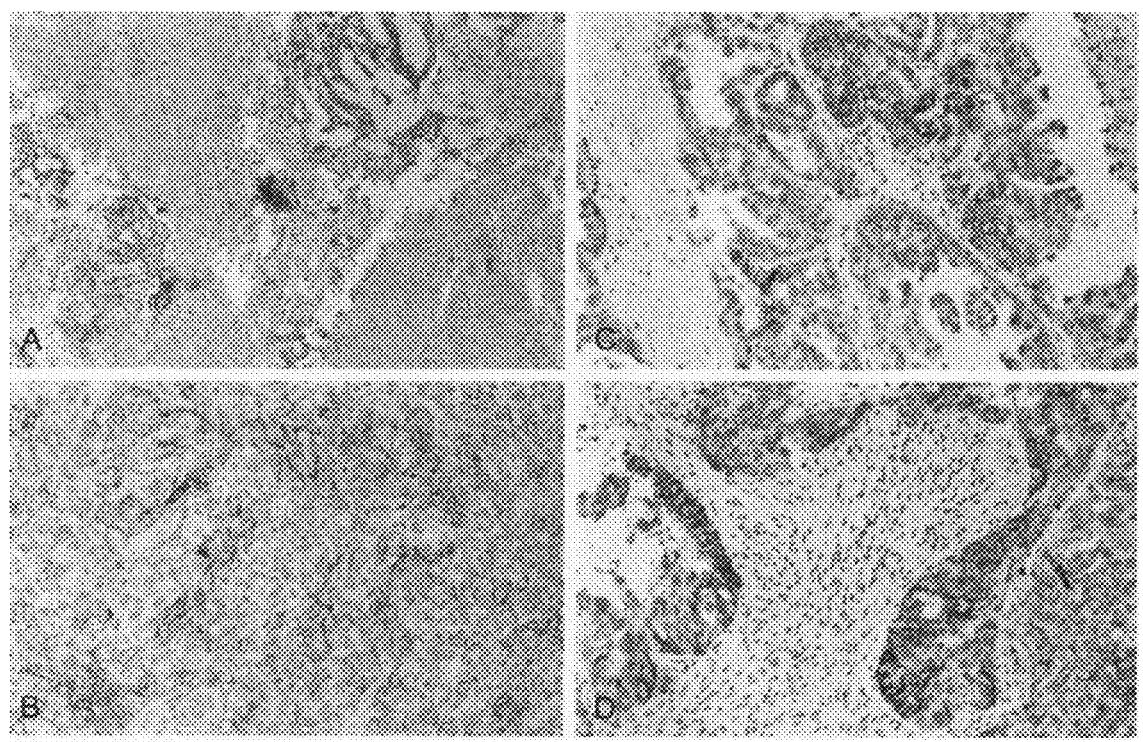
FIG. 2: Detection of L1 from curettage material.

FIG. 2 shows that L1 can also be detected by means of curettage tissue. Using the above described procedure, a similar staining pattern as on the tumor sections results. The determination of L1 by means of curettage material permits an early preoperative classification of the tumor within the meaning of Tables 1 and 2.

Example 2

ELISA Shows the Presence of Soluble L1 in Sera and Ascitic Fluid of Tumor Patients, a Correlation Between the Presence of L1 and the Tumor Type (Ovarian and Endometrial Tumor) being Observed Samples of body fluids (ascites, serum) were tested for the presence of soluble L1 using a "capture" ELISA. For this purpose, microtitration plates were coated with the human anti L1 antibody (concentration: 1 µg/ml) described in Example 1 and then a blocking step was carried out with 3% BSA in PBS (45 min., room temperature) to eliminate the non-specific bonding to the plate. The body fluid was added at differing concentrations (1:2 and 1:10 of the fluid in 3% BSA in PBS), and incubation was carried out at room temperature for 1 hour. Therefore, four wash steps followed in Tris-buffered common salt solution (TBS, pH 8.0, in the presence of 0.02% Tween-20). Bound soluble L1 was determined by the addition of human biotin-conjugated anti L1 antibody. For this purpose, the biotinylated antibody MCA1753 is added to the microtitration plates for 1 hour. This was followed by 4 wash steps as described above. Another incubation at room temperature for 1 hour with peroxidase-conjugated streptavidin (Dianova Hamburg, Germany) follows. Finally, another 4 wash steps are carried out.

Figure 3:
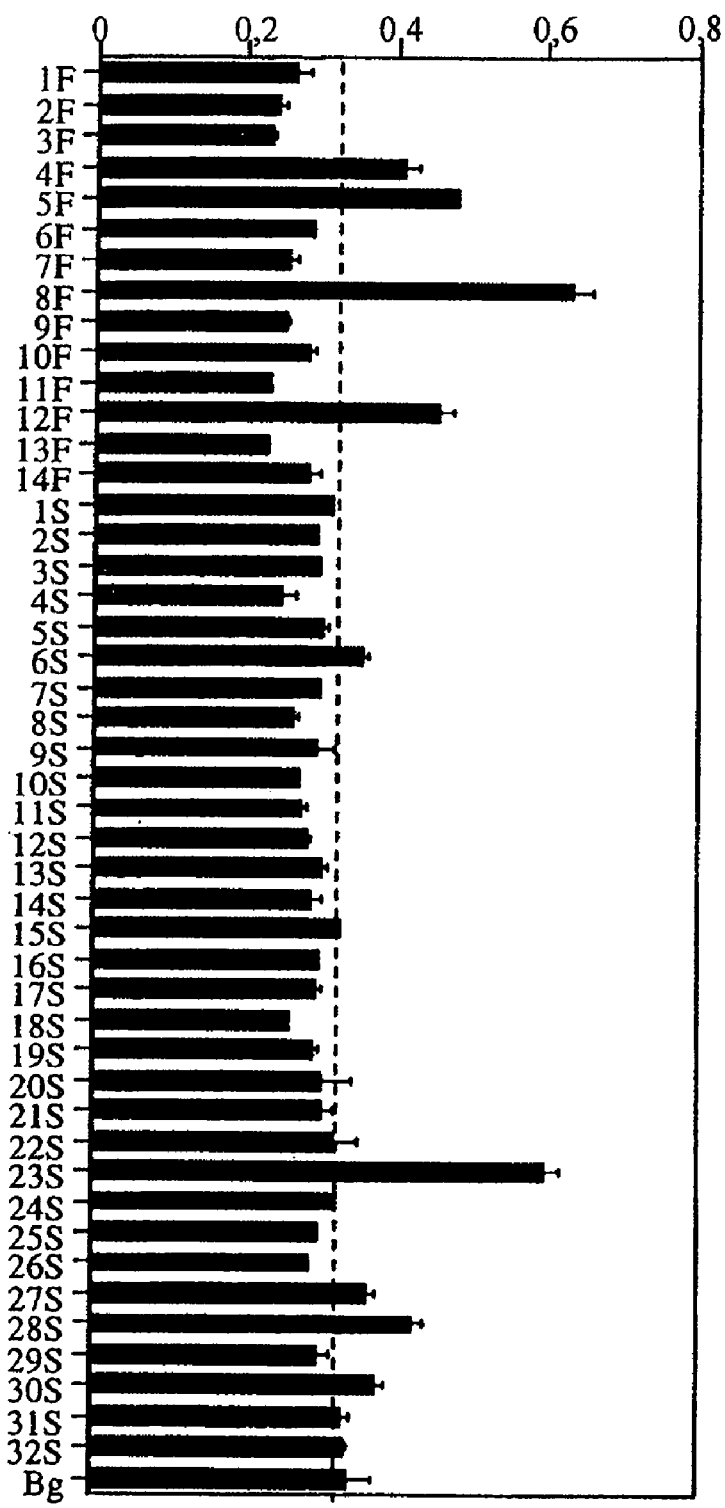
FIG. 3: Detection of soluble L1 in body fluids (1F-14F) and sera (1S-32S) by means of ELISA. The samples 4F, 5F, 8F, 12F and 23F originate from female ovarian cancer patients.
Figure 4:
FIG. 4: 1%-Agarose gel after PCR analysis of exon 27 usage. mRNAs from ovarian tumor speciments or known tumor cell lines (AR, OAW, Mel63) were isolated and transcribed in cDNA. These cDNAs were used as template for PCR analysis of exon 27 usage, Plasmids encoding both forms were used as control (−RSLE/+RLSE).

Hereinafter the substrate solution is added to the microtitration plates and upon appearance of the color reaction the result is evaluated on the ELISA reader. The results are shown in FIG. 3.

Example 3

A New ELISA Format for the Detection of Soluble L1

Figure 5A:
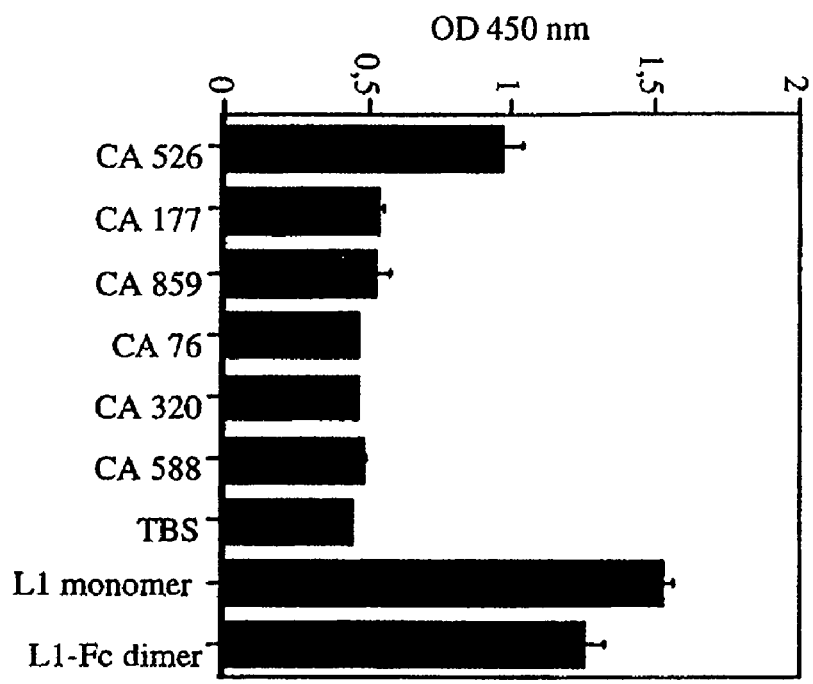
FIG. 5A: Microtiter plates were coated with L1 mAB 1 followed by blocking with 3% BSA/TBS and incubation with patient sera as described in Example 2. Bound soluble L1 was detected using biotinylated L1 mAB followed by Streptavidin-Peroxidase. This ELISA format can detect dimeric (multimeric) and monomeric L1.
Figure 5B:
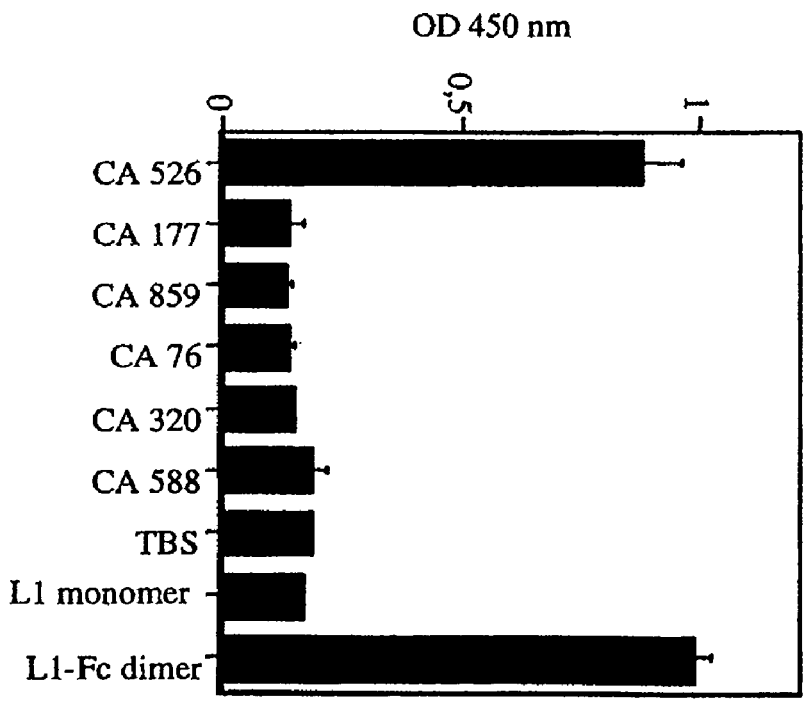
FIG. 5B: The ELISA was carried out as described in A but bound soluble L1 was detected using L1 mAB 1 followed by Streptavidin-Peroxidase. This ELISA format can detect only dimeric (multimeric) L1.
Figure 6A:
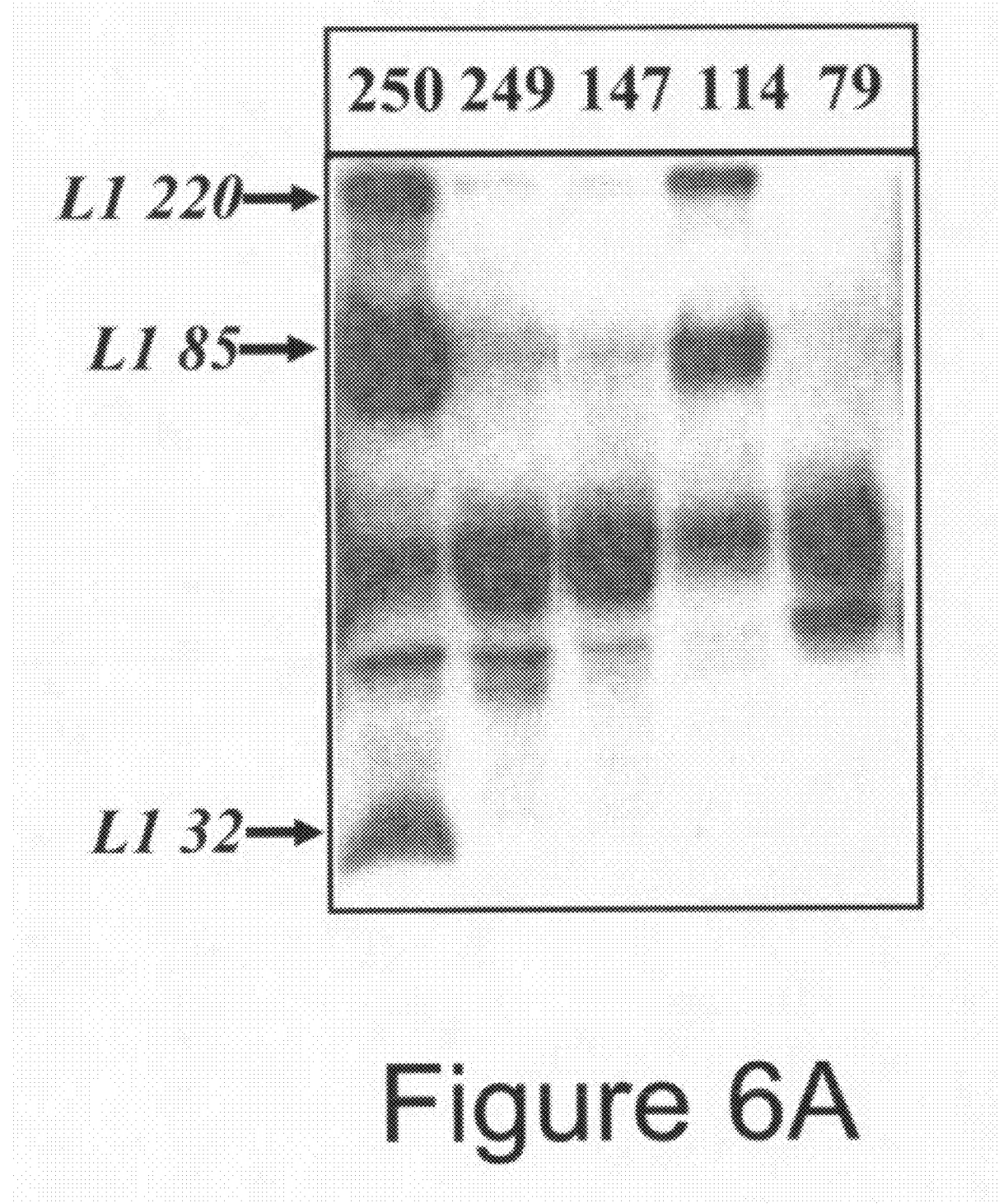
FIG. 6A: Ovarian tumor specimens were lysed and analysed by SDS-PAGE and Western blotting using an antibody to the cytoplasmic portion of L1.
Figure 6B:
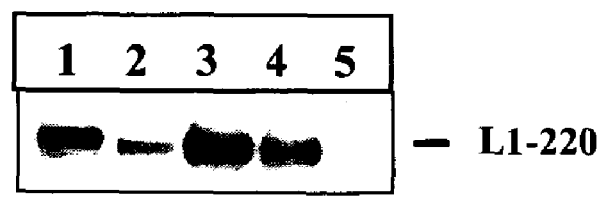
FIG. 6B: Sera from tumor patients were immunoprecipitated with L1 antibody coupled to sepharose, separated by SDS-PAGE and analysed by Western blotting using the same anti L1 antibody.
Figure 6C:
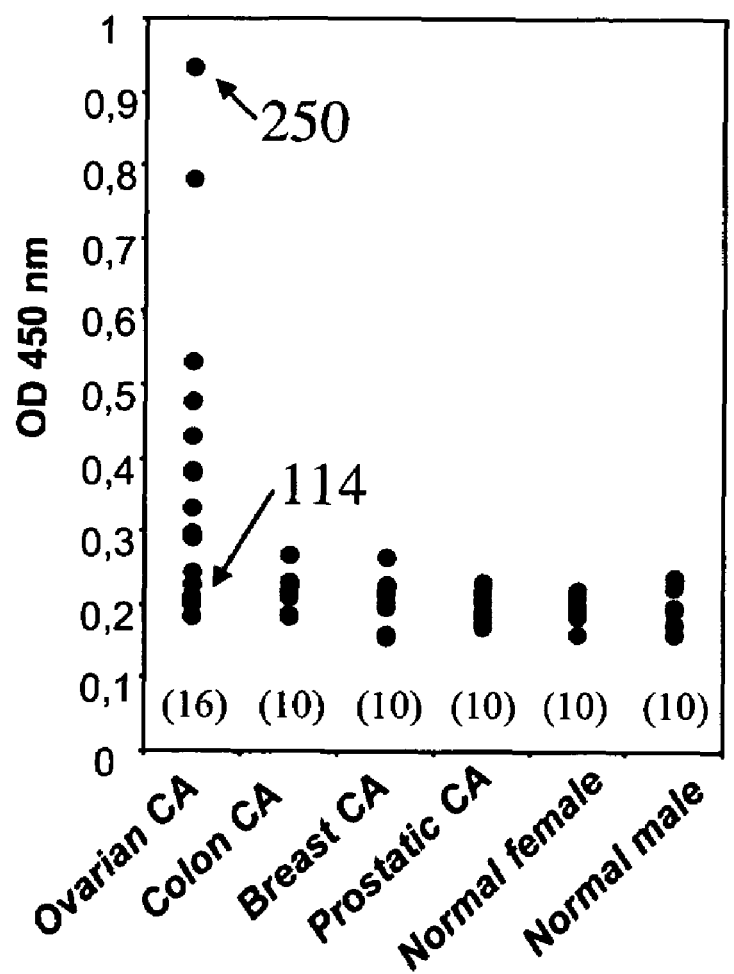
FIG. 6C: Sera of tumor patients and normal individuals were analysed by ELISA for the presence of soluble L1. The number of patients from each group is indicated in brackets.

The ELISA described above in Example 2 used the coating of the microtiter plate with L1 mAb 1 (capturing monoclonal antibody) and the detection of soluble L1 with a biotinylated (or otherwise labelled) L1 mAb 2 (detecting monoclonal antibody). This type of ELISA is termed G/K format. We have now developed another format in which we use both for capturing and detection the same mAb to L1 (K/K format). In FIGS. 5 A and B a comparison of both types of ELISA is shown using a positive serum (CA526, ovarian tumor patient) and seval control sera from unrelated tumors. It is obvious that the new ELISA format in FIG. 5B gives a better signal to noise ratio (appr. 5-8 fold) than the previous format shown in FIG. 5A. As the K/K format can only work when the antibody epitope for detection is not blocked by the antibody used for capturing, these results implicate that in the serum sample the soluble L1 is dimeric or multimeric. The control data performed in FIG. 5 with both types of ELISA using monomeric and dimeric L1 (the L1-Fc fusion protein is dimeric) support this notion.

Example 4

PCR Analysis for Detecting L1 mRNA in Tumor Samples

Primer sequences for PCR analysis are deduced from the human L1 cDNA sequence (EMBL accession number M 74387). For the detection of human mRNA encoding L1 in tumor tissue or patient serum samples mRNA is isolated using commercial kits (Roche Molecular Biochemicals) and transcribed into cDNA. A nested PCR approach is used with the following primer combinations: First amplification primer 1: ACTGAGGGCTGGTTCATC (SEQ ID NO: 8) (sense), primer 2: CTTGCACTGTACTGGCCA (SEQ ID NO: 9) (antisense) (one cycle 45 sec, 94° C., 30 cycles of 1 min at 94° C., 1 min at 56° C., 1 min at 72° C.). For the second PCR 1 up of the first PCR reaction is used with primer 1: ACTCAGTGAAGGATAAGGAG (SEQ ID NO: 10) (sense), primer 2: TTGAGCGATGGCTGCTGCT (SEQ ID NO: 11) (antisense). In an alternative protocol the following primers are used: primer 1: AGGTCCCTGGAGAGTG (SEQ ID NO: 12) (sense); primer 2: TTGAGCGATGGCTGCTGCT (SEQ ID NO: 11) (antisense). The temperature profile for the PCR reaction are as described above. PCR products are preferably separated on a 2% agarose gel containing 0.5 μg/ml ethidium bromide. As an alternative, the gel is blotted and hybridized with the labeled L1 oligonucleotide probe (TCTGAGGC-CCGACCGATGAAAGATGAGACCTTC (SEQ ID NO: 13)) by southern blotting to increase the sensitivity.

TABLE I

Ovarian carcinomas

| Case No | Histological type | Histological grade | Seedeing to serosal surface | Seeding to omentum | Distant metastases | Clinical stage | Follow up (month) | Reccurance | Outcome | L1 staining |
|---|---|---|---|---|---|---|---|---|---|---|
| 1 | Serous | moderate-poorly | + | + | — | IIIc | 9 | | AWD | + |
| 2 | " | poorly | + | + | Lung Breast | IIIc/IV | 1 | | DOD | + |
| 3 | " | moderate-poorly | + | + | Brain | IV | 24 | + | DOD | + |
| 4 | " | moderate-poorly | − | + | — | IIIc | 36 | + | DOD | + |
| 5 | " | poorly | + | + | — | IIIc | 26 | + | DOD | + |
| 6 | " | moderate-poorly | − | + | — | IIIc/IV | 35 | + | DOD | + |
| 7 | " | moderate-poorly | + | + | — | IIIc | 22 | + | DOD | + |
| 8 | " | well | + | − | — | Ic | 22 | − | NED | − |
| 10 | " | poorly | − | + | — | IIIc | 62 | + | DOD | + |
| 11 | " | poorly | + | + | Lung Liver | IIIc/IV | 18 | + | DOD | + |
| 13 | " | poorly | − | − | — | Ic | 77 | − | NED | − |
| 14 | " | poorly | + | − | Liver | IIIc | 5 | − | AWD | + |
| 15 | " | poorly | + | − | — | IIIc | 11 | − | AWD | + |
| 16 | " | moderate | + | − | | III | | No information | | + |
| 24 | " | moderate | + | − | Lung | IV | 21 | + | AWD | + |
| 17 | Emdometroid | moderate | − | − | — | Ic | 20 | − | NED | − |
| 18 | " | poorly | − | − | — | Ic | 54 | − | NED | − |
| 19 | " | poorly | − | − | — | Ic | 55 | − | NED | − |
| 20 | " | moderate | − | − | — | Ic | 26 | − | NED | − |
| 21 | " | moderate | − | − | — | Ia | 45 | − | NED | − |
| 22 | " | poorly | − | − | — | Ib | 38 | − | NED | − |
| 23 | " | moderate | − | + | — | IIIc | 6 | − | AWD | + |
| 25 | " | moderate | + | + | — | IIIc | | No information | | + |
| 26 | " | poorly | + | − | Liver | IIIc | 35 | − | DOD | + |
| 27 | " | moderate | − | − | Vagina | IIIc | 12 | + | DOD | + |
| 28 | " | poorly | + | + | Lung | IV | 20 | − | AWD | + |
| 29 | " | poorly | + | + | — | IIIc | 17 | + | DOD | + |
| 30 | " | poorly | + | + | Lung | IV | 6 | + | AWD | + |
| 31 | " | moderate-poorly | + | + | — | IIIc | | No information | | + |
| 32 | " | moderate | + | + | — | Ic | 35 | − | NED | + |

AWD: alive with disease
DOD: died of disease
NED: no evidence of disease

TABLE II

Uterine carcinomas

| Case No | Histological type | Histological grade | Seeding to serosal surfaces amd omentum | Adnexal involvement | Clinical stage | Follow up (month) | Reccurance | Outcome | curretage | L1 staining endometrium | ovary |
|---|---|---|---|---|---|---|---|---|---|---|---|
| *1 | Emdometroid | poorly | + | + | IIc | ? | + | DOD | ND | + | + |
| 2 | " | moderate | + | + | IV | 21 | + | DOD | ND | + | + |
| 3 | Serous | poorly | + | + | IIIc | No information | | | + | + | + |
| 4 | " | poorly | + | + | III | " | | | + | + | + |
| 5 | " | moderate | + | + | * | " | | | ND | + | + |
| 6 | " | poorly | + | + | * | " | | | + | + | + |
| 7 | " | poorly | + | + | IV | 10 | + | DOD | ND | + | + |
| 8 | " | poorly | + | + | IV | 5 | + | DOD | + | + | + |
| 9 | " | poorly | + | + | IIIc | 26 | + | DOD | ND | + | + |
| 10 | " | moderate -poorly | + | + | IIIc | 22 | + | DOD | ND | + | + |

TABLE II-continued

Uterine carcinomas

| Case No | Histological type | Histological grade | Seeding to serosal surfaces amd omentum | Adnexal involvement | Clinical stage | Follow up (month) | Reccurance | Outcome | curretage | L1 staining endometrium | ovary |
|---|---|---|---|---|---|---|---|---|---|---|---|
| 11 | " | poorly | – | – | Ib | 6 | – | NED | – | – | – |
| 12 | " | moderate -poorly | – | – | Ic | 28 | – | NED | – | – | – |

\* Only two cases of endometroid-type uterine carcinomas with advanced stage with the involvement of the adnexa and are shown in Table 2. These tumors were positive for L1 in the endometrium and the ovary and the patients had a bad prognosis. Additionally, 38 patients with endometroid-type tumors were studied all of which were in low clinical stage, were negative for L1 and had a good prognosis (follow-up between 8-54 months).

The invention claimed is:

1. A method of treating ovarian or endometrial tumors in a patient in need of such treatment, said method comprising administering to the patient a sufficient amount of a L1 antibody or fragment thereof conjugated to a cytotoxic drug, wherein the sufficient amount of the L1 antibody or fragment thereof is an amount sufficient to kill cells within the ovarian or endometrial tumors being treated and wherein the L1 antibody fragment has the same epitope specificity as a complete L1 antibody.

2. The method of claim 1, wherein the cytotoxic drug is selected from among radionuclides, toxic proteins, saporin, and chemotherapeutic agents.

* * * * *

```
                        SEQUENCE LISTING

<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

Ala Thr Glu Gly Trp Phe Ile Gly Phe
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Gly Ser Asp Asp Ser Leu Ala Asp Tyr
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Leu Leu Ala Asn Ala Tyr Ile Tyr Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Trp Leu Asp Glu Asp Gly Thr Thr Val
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Val Leu Thr Gly Tyr Val Leu Ser Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Ala Gln Tyr Ile Lys Ala Asn Ser Lys Phe Ile Gly Ile Thr Glu Leu
1               5                   10                  15

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
aggctgtcgt cactgccca                                            19

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
actgagggct ggttcatc                                             18

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
cttgcactgt actggcca                                             18

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
actcagtgaa ggataaggag                                           20

<210> SEQ ID NO 11
<211> LENGTH: 19
<212> TYPE: DNA
<213> ORGANISM: Artificial Sequence
```

```
-continued

<220> FEATURE:
<223> OTHER INFORMATION: Synthetic Construct

<400> SEQUENCE: 11
ttgagcgatg gctgctgct                                                    19

<210> SEQ ID NO 12
<211> LENGTH: 16
<212> TYPE: DNA
<213> ORGANISM: Artificial Sequence
<220> FEATURE:
<223> OTHER INFORMATION: Synthetic Construct

<400> SEQUENCE: 12
aggtccctgg agagtg                                                       16

<210> SEQ ID NO 13
<211> LENGTH: 33
<212> TYPE: DNA
<213> ORGANISM: Artificial Sequence
<220> FEATURE:
<223> OTHER INFORMATION: Synthetic Construct

<400> SEQUENCE: 13
tctgaggccc gaccgatgaa agatgagacc ttc                                    33
```